(12) United States Patent
Prime (10) Patent No.: US 6,470,756 B1
(45) Date of Patent: Oct. 29, 2002

(54) SYSTEM AND METHOD FOR MEASURING RESIDUAL STRESS

(75) Inventor: Michael B. Prime, Los Alamos, NM (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/792,840

(22) Filed: Feb. 23, 2001

(51) Int. Cl.$^7$ ................................................ G01N 19/08
(52) U.S. Cl. ........................................... 73/799; 73/804
(58) Field of Search ........................ 73/787, 791, 795, 73/799, 800, 804, 805, 806

(56) References Cited

U.S. PATENT DOCUMENTS

| | | | |
|---|---|---|---|
| 4,567,774 A | * 2/1986 | Manahan et al. | 374/49 |
| 5,345,490 A | * 9/1994 | Finnigan et al. | 345/420 |
| 5,432,595 A | 7/1995 | Pechersky | 356/35.5 |
| 5,920,491 A | * 7/1999 | Hibbitt et al. | 700/97 |
| 6,155,104 A | 12/2000 | Suresh et al. | 73/81 |
| 6,237,303 B1 | * 5/2001 | Allen et al. | 52/653.1 |

OTHER PUBLICATIONS

Michael B. Prime and Antonio R. Gonzalez; The Contour Method: Simple 2–D Mapping of Residual Stresses; Sixth International Conference on Residual Stresses, Jul. 10–12, 2000, Oxford, UK; pp. 617–625.

Michael B. Prime; The Contour Method: Simple 2–D Mapping of Residual Stresses; International Mechanical Engineering Conference and Exposition, Nov. 5–10, 2000, Orlando, Florida; pp. 121–127.

Michael B. Prime; Cross–Sectional Mapping of Residual Stresses by Measuring the Surface Contour After a Cut; Journal of Engineering Materials and Technology; pp. 162–168, Apr. 2001.

Michael B. Prime; Residual Stress Measurement by Successive Extension of a Slot: The Crack Compliance Method; Appl Mech Rev vol. 52, No. 2, Feb. 1999; pp. 75–96.

J.F. Williams and D.C. Stouffer; An Estimate of the Residual Stress Distribution in the Vicinity of a Propagating Fatigue Crack; Engineering Fracture Mechanics, vol. 11, 1979; pp. 547–557.

(List continued on next page.)

*Primary Examiner*—Max Noori
(74) *Attorney, Agent, or Firm*—Madson & Metcalf (57) ABSTRACT

The present invention is a method and system for determining the residual stress within an elastic object. In the method, an elastic object is cut along a path having a known configuration. The cut creates a portion of the object having a new free surface. The free surface then deforms to a contour which is different from the path. Next, the contour is measured to determine how much deformation has occurred across the new free surface. Points defining the contour are collected in an empirical data set. The portion of the object is then modeled in a computer simulator. The points in the empirical data set are entered into the computer simulator. The computer simulator then calculates the residual stress along the path which caused the points within the object to move to the positions measured in the empirical data set. The calculated residual stress is then presented in a useful format to an analyst.

22 Claims, 4 Drawing Sheets

OTHER PUBLICATIONS

M.R. Johnson et al.; Calculation of Residual Stresses in Wheels From Saw Cut Displacement Data; The American Society of Mechanical Engineers, Presented at the Winter Annual Meeting, Miami Beach, Florida, Nov. 17–21, 1985.

M.W. Joerms; Calculation of Residual Stresses in Railroad Rails and Wheels from Sawcut Displacement; Proceedings of ASM's Conference on Residual Stress—In Design, Process and Materials Selection, Cincinnati, Ohio, USA Apr. 27–29, 1987.

K.Y. Lin and J.S. Huang; Analysis of Residual Stresses in Railroad Car Wheels Based on Destructive Test Measurements; Theoretical and Applied Fracture Mechanics 12 (1989); pp. 73–86.

Terry L. Dickson et al.; The Inclusion of Weld Residual Stress in Fracture Margin Assessments of Embrittled Nuclear Reactor Pressure Vessels; The 1998 ASME/JSME Joint Pressure Vessels and Piping Conference, San Diego, California, Jul. 26–30, 1998; 387–391.

Michael B. Prime and Antonio R. Gonzales; The Contour Method; Simple 2–D Mapping of Residual Stresses; Los Alamos National Laboratory, LA–UR–00–1900; pp. 1–9.

Michael B. Prime; The Contour Method: Simple 2–D Mapping of Residual Stresses; Los Alamos National Laboratory LA–UR–00–1900; pp. 1–65.

Michael B. Prime; Cross–Sectional Mapping of Residual Stresses by Measuring the Surface Contour After a Cut; Los Alamos National Laboratory LA–UR–00–205; pp. 1–25.

Robert P. Currier; The Plasma Fluidized Bed; Los Alamos FY 1999 LDRD Progress Report; p. 1.

Michael Prime; The Compliance Method for measuring Residual Stress; Los Alamos FY 1999 LA–13730–PR Progress Report; p. 1.

* cited by examiner

SYSTEM AND METHOD FOR MEASURING RESIDUAL STRESS

GOVERNMENT RIGHTS STATEMENT

This invention was made with Government support under Contract No. W-7405-ENG-36 awarded by the United States Department of Energy to The Regents of the University of California. The Government has certain rights in the invention.

BACKGROUND OF THE INVENTION

1. Field of the Invention

The present invention relates to methods for measuring stress within an object. More specifically, the invention relates to a method for determining residual stress within materials.

2. Relevant Technology

The composition of natural and man made materials is well understood. We know that materials are made up of atoms that are bonded by atomic forces to form solids. Atoms may also combine with other atoms to form molecules. These molecules may be bonded closely together, as with solids, or far apart, as with gases. The state of the material, solid, liquid, or gas, depends on the amount of energy the molecules have. Because molecules and atoms have no known structural connection, they are free to move and act in response to the attraction forces of the molecules and atoms around them. These attraction forces may be conceptualized as very small springs which connect each atom, and/or molecule. The strength or weakness of the attraction forces depends largely on the amount of energy the atom is exposed to. Because the molecules and atoms of an object are exposed to different amounts of energy atoms at one location within an object may be pulled or pushed by other atoms.

These push and pull forces are known as stress. Stress is a force divided by an area. The force is the atomic attraction force and the area is a measured area of an object. In common elements such as iron or copper, the atoms are atomically bond together in a very tight lattice. Because different atoms of an object are exposed to varying amounts of energy, the stress of one or more atoms on neighboring atoms varies throughout the material. The different magnitudes of stress throughout an object are known as residual stress.

The name comes primarily from the fact that residual stress is the stress remaining within an object as a result of forming, shaping or otherwise processing the object. Generally, objects are formed by exposure to a change in energy, or heat, and an application of pressure. For example, diamonds are carbon atoms which have undergone extreme heat and pressure. The heat and pressure apply stress to the diamond. When the heat and pressure are removed, the atoms making up the diamond react by pulling and pushing each other. The push and pull within the diamond is residual stress, the stress left after application of the formation stress.

Similarly, man made objects experience some form of processing before the final product or object is ready for use. Particularly with metals, there are a number of processing methods which may be used to form, shape and refine the elements into metallic objects made of one element or composite objects made of two or more elements. For example, steel is made from combining iron and carbon. Other steel alloys are made using iron, carbon, and other natural or man made elements. Processing methods for creating steel or other metallic alloys include, forging, case hardening, quenching, welding, bonding, casting, extruding, and the like. These methods involve heating the elements and applying pressure to shape the object. From steel other objects may be created. These objects may require that the steel be rolled, hammered, stamped, drilled, machined, or otherwise shaped.

Whenever an object is exposed to a change in temperature, or application of pressure, the atoms within the object react by increasing or decreasing their attraction on neighboring atoms. This changes the residual stress within the object. Residual stress may not be a major concern in large applications of an object, such as the blade of a shovel. But, residual stresses contributes to failures from fatigue, fracture, distortion, wear, creep, stress corrosion cracking and the like. Material may also be processed to make parts of machines where a variation in size or performance of a part may cause serious problems.

For example, military fighter planes are generally made of metal and metal alloy parts. Due to the stress and change in temperature operation of the fighter places on the parts, the parts are precision machined and engineered to exact specifications. The problem is the residual stresses within a part may cause the part to distort, or deform during use, or prior to installation such that the part is unusable. This may be very costly. One estimate suggests that the cost of distorted scrapped fighter plane parts is around $263 million.

Techniques do exist for calculating the residual stress within an object. In the hole drilling method, a strain gauge rosette is placed on a free surface of the object. Then, a hole is drilled in the middle of the rosette. The strain gauge rosette is then used to measure the strain of the surface once the hole is cut. In the layer removal method, changes in one existing surface are measured after a layer of material is removed from an opposite surface. In the compliance method, the strain is measured near or opposite a successively extended slot. Other techniques such as Moire interferometry also exist.

These techniques as well as the method of the present invention, relate to elastic materials. Elastic materials are those which deform in response to internal or external stresses placed on the object. All materials are elastic to some degree. These techniques measure the residual stress by calculating how much the material deformed after some of the material is removed through removing a layer, drilling a hole, and the like. The material deforms once a hole or other material is removed because the residual stress within the material is freed through creation of the hole, cut, or layer.

These techniques are related because each performs the measurements on a pre-existing surface of the object. The problem is that measuring a change in a pre-existing surface is not as precise as measuring the new free surface created by cut, hole, or layer removal. Because stress is not being released at the pre-existing surface, any changes in the pre-existing surface are approximations of the deformation at the newly created surface which caused the measured deformation at the pre-existing surface. In other words, the accuracy of measurements taken at a pre-existing surface is limited due to the remoteness between where the residual stress is relieved and where the measurements are made.

Additionally, because the measurements are indirect representations of the displacement at the newly formed surface, the calculations to arrive at the residual stress at the newly created surface are complex. The calculations involve theoretically complex and tedious inversion calculations simply to determine the residual stress in a single dimension. Completing the calculations and reducing the measurements to the residual stresses may take several weeks, particularly if an analyst needs to know the residual stress in two or three dimensions.

Measuring the new free surface would allow one to calculate the residual stress which existed prior to removal of the material. However, there is not a reference point which may be used to determine the amount of change in the new free surface after the material is removed. In addition, other techniques may avoid measuring deformation at the new free surface because the drill bit, or cutting tool introduced residual stress into the material during the removal process.

Therefore, it would be an advancement in the art to provide a system and method for determining the residual stress within an elastic object at a new free surface where the residual stress is being relieved. It would be a further advancement to provide a system and method for determining the residual stress within an elastic object such that the calculations are simple and direct rather than inversion calculations involving complex theory. It would be another advancement in the art to provide a system and method for determining the residual stress within an elastic object such that an analyst does not need special training or expertise to perform the measurements.

SUMMARY OF THE INVENTION

The invention is a system and method for determining the residual stress within an elastic object. The method includes measurements of a real world object as well a computer model of the object.

First, an elastic object is cut through a path. Preferably, the path is a plane having a known location and perpendicular orientation with respect to the object. The cut is preferably made using a tool which introduces minimal residual stress into the object. The cut creates a new free surface on either side of the cut. Due to the elasticity of the object and the residual stress, the free surface deforms once the cut is made.

Next, one of the two free surfaces is measured to identify a contour of the new free surface. The contour measures the deformation of the free surface from the path. This deformation or displacement represents the amount of relief in the free surface caused by the residual stress after the cut is made. The contour is defined by points measured in a direction parallel to the path. These points represent areas of deformation on the free surface. The contour may be measured in one, two, or three dimensions The measurements are recorded in an empirical data set.

Then, a model of a portion of the object which includes the free surface is created in a computer simulator. The computer simulator may employ the finite element method (FEM). These computer simulators may also be known as FEM simulators. Using the FEM simulator, a model of the portion of the object is created to represent the portion of the real object which includes the measured free surface.

The model of the portion may be defined by a finite set of elements which interconnect to define the portion. The portion as a whole and each of the elements of the portion act in relation to boundary conditions. A boundary condition is a type of force or constraint which may be applied to the portion. A plurality of boundary conditions may act on a portion at any given time.

Boundary conditions are generally defined for the whole exposed surface of the portion. The FEM simulator then applies the boundary conditions to each element individually. Boundary conditions may be of various types including a force, a moment, a distributed load and the like. For each of these types of boundary conditions different properties of the portion may be defined. For example a moment boundary condition may require that the force and the moment arm be defined. A force boundary condition may require a value for the force and an indication of where on the portion the force acts.

Generally, a set of initial conditions are defined for an object at the time the object is created. An FEM simulator allows initial conditions to be defined for known residual stress within an object. In a preferred embodiment, no initial conditions are defined to model residual stress. Alternatively, the present invention may be practiced with initial conditions which define residual stress.

The steps of defining the equilibrium equations and applying these equations to each element may be referred to as initialization. Initialization includes defining properties for individual elements in the model. These properties may include the modulus of the material, the poisson ratio, and the kind of material which makes up the portion.

If an elastic material is cut, material is removed, then the new free surface deforms due to the residual stresses. Under Bueckner's superposition principle, if the free surface is returned to its position prior to deformation, the difference between the original position and the new deformed position may be used to determine the residual stress at that point prior to the cut. The residual stress caused the point to change position. Using the empirical data set and the FEM simulator, the superposition principle is applied.

The empirical data is entered into the FEM simulator. The empirical data represents the position of points along the free surface in a x, y, and z axis coordinate system related to the real object. The empirical data is entered as a displacement boundary constraint having a different sign than that originally measured in relation to the path. The model portion has corresponding points along the free surface of the model.

Then, the FEM simulator calculates the residual stress by reviewing each element along the displacement boundary constraint to points along the path. The change in position and the properties of the elements of the portion are used by the FEM to calculate residual stress along the path. Using the path as a point of origin, the difference in sign indicates which direction the stress acts perpendicular to the path. The residual stress along the path is accumulated into residual stress data which may be directly examined, presented in a color coded stress map, or otherwise utilized by an analyst interested in the residual stress of the object.

One embodiment of the present invention may comprise the aforementioned method steps. It is understood that variations in the steps of the method or components of the system may be made and still come within the scope of the present invention. These and other features and advantages of the present invention will become more fully apparent from the following description and appended claims, or may be learned by the practice of the invention as set forth hereinafter.

BRIEF DESCRIPTION OF THE DRAWINGS

These and other more detailed and specific features of the present invention are more fully disclosed in the following specification, with reference to the accompanying drawings, in which.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the system, and method of the present invention, as represented in FIGS. 1A through 4, is not intended to limit the scope of the invention, as claimed, but is merely representative of presently preferred embodiments of the invention.

FIGS. 1A through 4 are block diagrams and a flow chart which illustrates in more detail certain embodiments of a system and method steps for carrying out the present invention. Although FIGS. 1A–1C and 3A–3C illustrate steps of the invention in two dimensions, determining the residual stress along a three dimensional surface is also within the scope of the present invention.

Figure 1A:
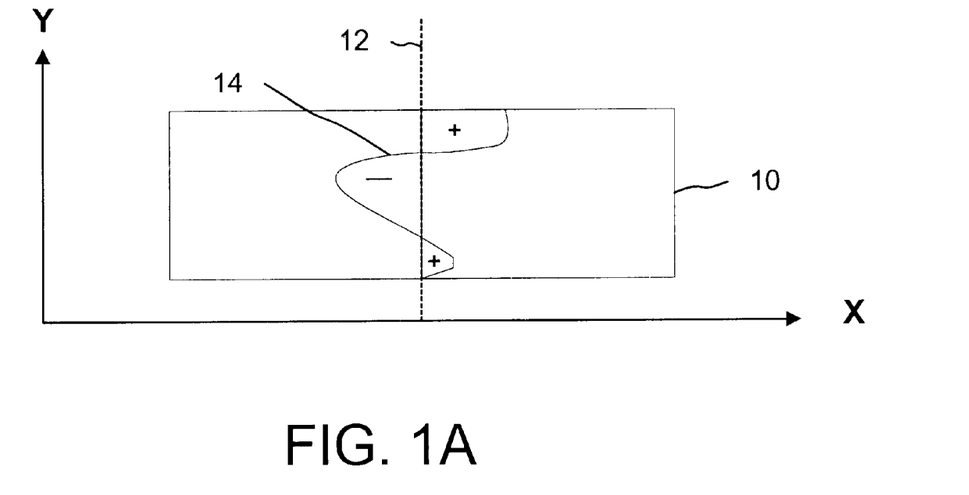
FIG. 1A is a block diagram illustrating areas of positive and negative residual stress within an object.

FIG. 1A is a block diagram illustrating a front elevation view of an object for which determination of the residual stress is desired. An object 10 of material is presented. The object 10 may be made of natural or synthetic materials. Preferably, the material is elastic and a metal alloy. Alternatively, the material may be a polymer, composite material, non-crystalline material, amorphous material, or other material of similar characteristics. Non-crystalline materials are those which do not comprise a crystalline structure at a molecular level.

It is desirable that the residual stress be determined within the object 10 along path 12. In the illustrated embodiment, path 12 is a plane illustrated by the dashed line. Therefore, path 12 is parallel to the y-axis and perpendicular to the x-axis. Alternatively, path 12 maybe a curved path 12 through the object 10.

Curve 14 represents the unknown residual stress distribution along path 12. The curve 14 indicates magnitudes of stress at points along path 12 by the sign and height of curve 14 in relation to path 12. For example, the negative sign and high peak of the curve 14 to the left of path 12 represents high residual stress along path 12 directed towards the left. The negative sign indicates residual stress compressing at those points along path 12. Similarly, the positive sign indicates tension stress along those points along path 12.

However, curve 14 represents the unknown residual stress which the analyst desires to determine. Determination of curve 14 may be accomplished by applying Bueckner's superposition principle. Under this principle, if elastic material containing residual stress is cut such that minimal residual stress is introduced, then the material will relax along the boundary of the cut in direct relation to the residual stress which is freed by the making of the cut. Therefore, if the amount of relaxation, or deformation may be measured with respect to the boundary of the cut, then the residual stress along the cut may be determined. This principle is illustrated by reference to FIGS. 1A, 1B, and 1C.

Figure 1B:
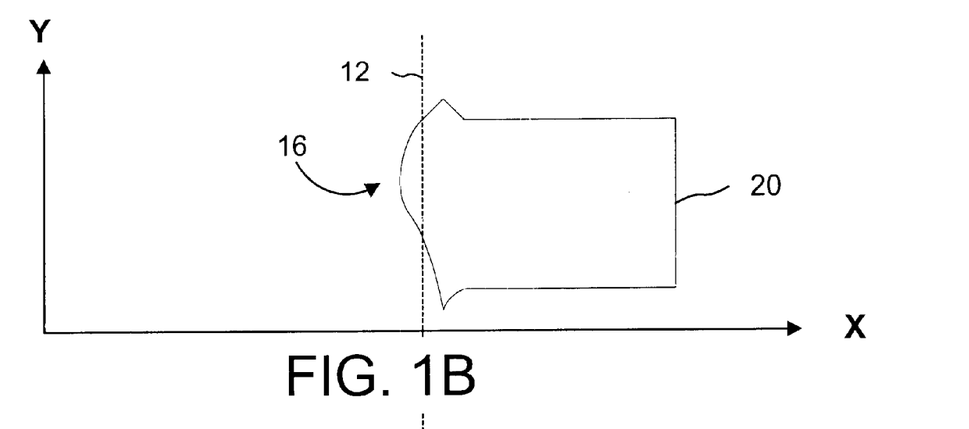
FIG. 1B is a block diagram illustrating a deformed free surface of the object in FIG. 1A after a cut is made.

In FIG. 1B, the object 10 is illustrated after being cut along path 12. The cut creates portion 20 having a new free surface 16, or contour 16 along the path 12. The cut allows the residual stress along path 12 to be released. Due to the elasticity of the portion 20, the contour 16 deforms. Deformation or displacement of the contour 16 is sometimes referred to as relaxation. The residual stresses which acted along path 12 prior to the cut deform the contour 16 until the residual stress along the path 12 reaches equilibrium, meaning no more displacement. The residual stresses along path 12 have relaxed.

Next, the contour 16 must be measured to calculate how much the free surface changed position in relation to path 12. Preferably, these measurements are made using a coordinate measuring machine (CMM). Alternatively, other measuring devices may be used to determine how the contour 16 has changed.

The CMM operates by defining a three dimensional space and fixing the object 10 within this space. Then a probe traverses the contour 16. The probe records the x, y, and z coordinate of where the probe contacts the contour 16 of the portion 20. These coordinates represent points along the surface of the contour 16. The points are recorded in an empirical data set. The empirical data set is a collection of the measured points indicating the position of the contour 16.

Figure 1C:
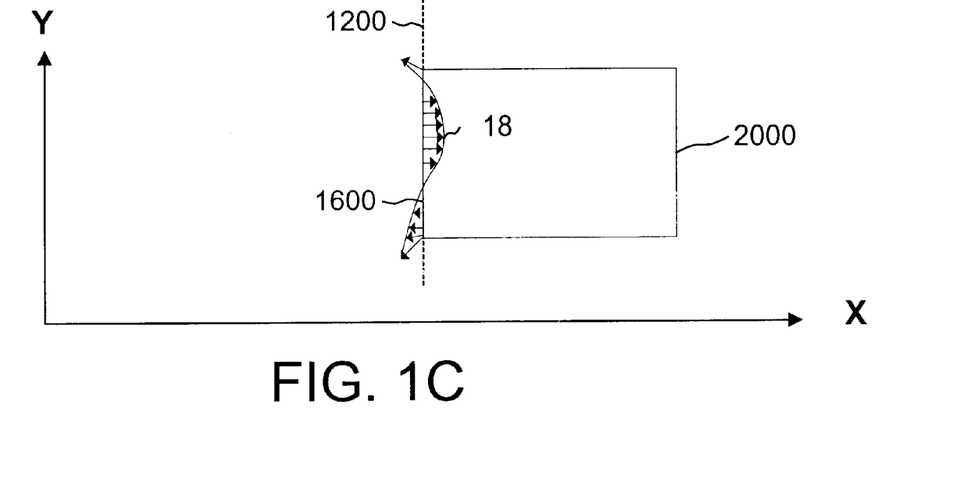
FIG. 1C is a block diagram illustrating displacements along the free surface of FIG. 1B which may be used to calculate residual stress within an object.

FIG. 1C illustrates how the empirical data set and a model of portion 2000 may be used to determine the original unknown residual stress curve 14 of FIG. 1A. Under the superposition principle the residual stresses acting normal to the y-axis, and path 12 is determinable because the displacement of the contour 16 with relation to the path 12 is known. From this displacement, the force, residual stress may be calculated.

FIG. 1C illustrates a modeled object portion 2000. The portion 2000 may be modeled in an FEM simulator. A path 1200 is also modeled. The path 1200 is in substantially the same position as path 12. Portion 2000 represents the cut portion 20 of FIG. 1B. However, portion 2000 is modeled without the displacement along path 1200 experienced by portion 20. The contour 1600 follows the path 1200. In an alternative embodiment, the whole object 10 may be modeled and then a cut simulated by removing a portion of the model object to one side of path 1200.

Modeling portion 2000 includes defining the size, material composition, modulus, and poisson ratio for the portion 2000. The modulus and poisson ratio define how the bonds (similar to springs) of atomic elements within the portion 2000 may be stretched or compressed together. As mentioned earlier, the portion 2000 is modeled using a finite set of elements having properties which relate directly to properties of elements in the real world object 10.

Referring still to FIG. 1C, in one embodiment, the portion 2000 is modeled having no residual stress. This is reasonable because the residual stress within portion 20 of FIG. 1B is unknown. However, due to relaxation, the residual stress normal to path 12 in portion 20 must be zero. The superposition principle indicates that the residual stress within FIG. 1A is equal to the residual stress along contour 16 in FIG. 2B added to the residual stress along contour 1600 in FIG. 2C. Knowing the residual stress along contour 16 in FIG. 2B is zero means once the residual stress along contour 1600 is determined that result will equal the residual stress along curve 14. As the residual stress normal to path 12 in FIG. 1A, is the desired result, beginning with no residual stress within portion 2000 is reasonable.

Alternatively, the residual stress within portion 2000 may be approximated by first approximating the residual stress within object 10. Additionally, different processing techniques applied to object 10 and/or portion 20 may allow an analyst to determine a very close approximation of the residual stress within object 10 and/or portion 20.

Next, referring specifically to FIG. 1C and generally to FIGS. 1A and 1B, the empirical data set is entered into the FEM simulator. The coordinate system of the CMM in relation to the portion 20 is substantially the same as the coordinate system used in the FEM simulation of portion 2000. Therefore, each point in the empirical data set generally corresponds to a point along path 1200 in the FEM simulator. Preferably, the empirical data set is entered by defining a displacement boundary condition in the FEM simulator. The displacement boundary condition marks a boundary 18 along path 1200 which a force has caused elements of the portion 2000 to change position such that they align with the boundary 18. The FEM simulator is then capable of determining the forces which caused the elements of portion 2000 to align with boundary 18. These forces are residual stress within the portion 2000. The FEM calculates the stress for all the elements of the portion 2000. However, because the portion 2000 was modeled without residual stress to begin with, a state which is almost impossible to achieve, the residual stress throughout the portion 2000 is inaccurate except for residual stress which acts normal to elements along path 1200.

Under the superposition principle, the residual stress within object 10 of FIG. 1A is equal to the residual stress along the free surface, or contour 16 in FIG. 1B plus the residual stress along path 1200 in FIG. 1C. Because contour 16 is a free surface, the residual stress normal to path 12 is zero. Therefore, the residual stress normal to path 1200 is equal to the residual stress within the object 10 in FIG. 1A. In this manner, the residual stress curve 14 has been determined.

In a preferred embodiment, described above, the residual stress determined is the residual stress in the x direction, or normal component of the residual stress. In an alternative embodiment, the residual stress may be determined in the y direction, or transverse normal component, and z direction. The same superposition principle may be applied. However, the residual stress in y and z directions are not known to be zero in FIG. 1B along contour 16. This is because material in portion 20 to the top, bottom, and sides of each point along contour 16 may impose residual stress on a point.

A preferred embodiment of the present invention may be used to determine the residual stress acting in the x direction, the normal component, the y direction, transverse normal, and z direction as in FIG. 1C. However, to determine the residual stress in FIG. 1A in the y and z directions the portion 20 in FIG. 1B must be measured for residual stress in the y and z directions. In an alternative embodiment, the residual stress may be determined in the y and z direction, or transverse normal component, and z direction through measuring techniques such as hole drilling or x-ray diffraction. The measured y and z residual stress may then be added to the residual stress in the y and z direction determined in FIG. 1C to find the residual stress in the y and z direction in FIG. 1A.

To complete the steps of the illustrated embodiment, the residual stress normal to path 1200 in FIG. 1C may be combined to form residual stress data. Residual stress data may comprise magnitudes and directions of residual stress force for each element along path 1200. The residual stress data may be presented to an analyst as a color coded image in which different colors indicate different magnitudes of residual stress at various points along path 1200. Alternatively, the residual stress data may report the residual stress data across the surface of portion 2000, 20 defined by path 1200, 12. The residual stress data may be analyzed directly or in various other types of data formats.

Figure 2A:
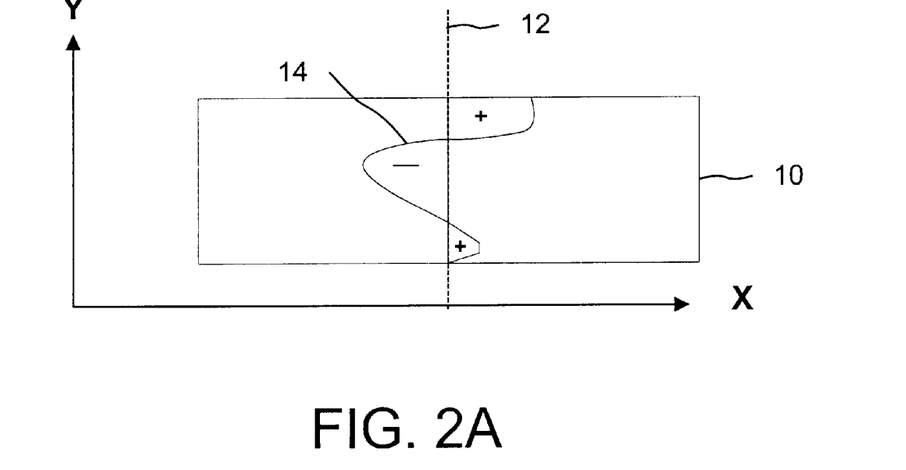
FIG. 2A is a block diagram illustrating areas of positive and negative residual stress within an object used in an alternative embodiment of the invention.
Figure 2B:
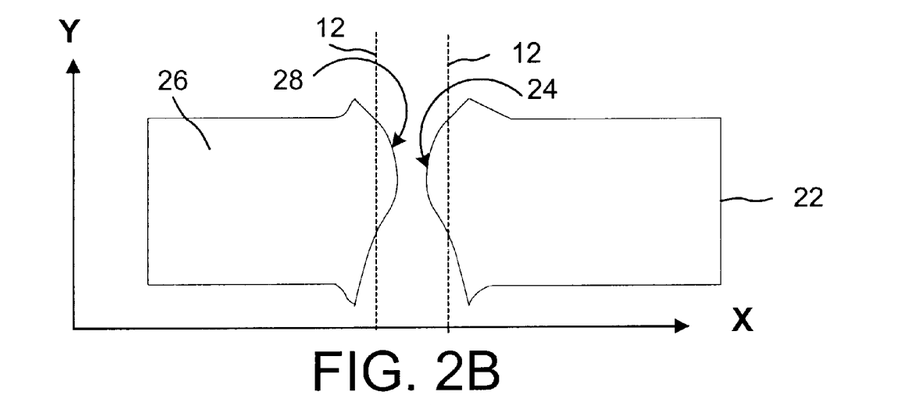
FIG. 2B is a block diagram illustrating a first and a second deformed free surface of two portions of the object in FIG. 2A after a cut is made.
Figure 2C:
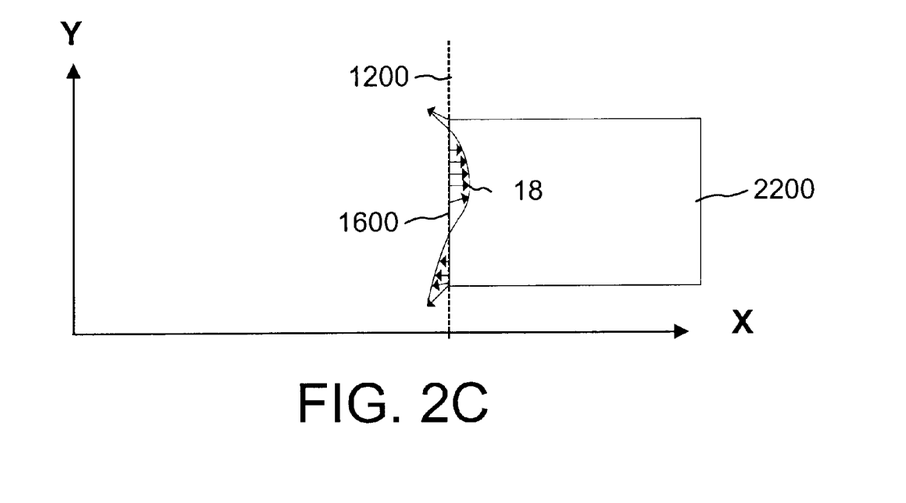
FIG. 2C is a block diagram illustrating the residual stress computed from the average deformation of the first and second free surfaces in FIG. 2B.

Referring now to FIGS. 2A, 2B, and 2C an alternative embodiment of the present invention is illustrated. FIG. 2A illustrates an elastic object 10 for which an analyst desires to determine the residual stress along path 12. As in FIG. 1A, curve 14 represents the unknown residual stress within object 10.

In FIG. 2B, the object 10 is cut and allowed to relax along path 12. Preferably, the path is along a plane. The cut creates a first portion 22 having a first free surface 24 and a second portion 26 having a second free surface 28. The first free surface 24 and second free surface 28 take a shape different from the path 12.

Now, a measuring device such as the coordinate measuring machine (CMM) used in FIG. 1B measures both first free surface 24 and second free surface 28. The CMM measures areas of deformation across first free surface 24 and second free surface 28. These areas of deformation may be represented by coordinate points indicating where areas of the first free surface 24 and second free surface 28 are in relation to the first portion 22 and second portion 26. Note in FIG. 2B there are two dashed lines indicating path 12. First portion 22 and second portion 26 are illustrated having a distance of separation for clarity. However, first free surface 24 and second free surface 28 are measured using the same path 12 as a reference.

Generally, for each area of deformation, or point, on the first free surface 24 there is a corresponding area of deformation, or point on the second free surface 28. As in FIG. 1B, the areas of deformation, or points are recorded in an empirical data set. However, in FIG. 2B each measured point on first free surface 24 is averaged with the corresponding measured point on second free surface 28.

Averaging the points may be implemented in different ways. In one embodiment, the first portion 22 may be positioned within an x, y, z axes and a plurality of points measured across first free surface 24. Then, second portion 26 may be positioned such that its x, y, and z axes matches that of the first portion 22. Then, points are measured across second free surface 28. Because the axes of first portion 22 and second portion 26 match up, the points measured may be compared. Next, the CMM or a computer process may review each measured point from first portion 22 and its corresponding point from second portion 26. The average of each point's position in the x, y, and z axes is then determinable because the axes have the same 0, 0, 0 point of origin. These averages may be recorded in the empirical data set. By averaging the measurements, errors introduced by the wire EDM may be reduced. Other errors, such as errors caused by residual shear stress, and errors due to movement of the object in relation to the path 12 as the cut is made may also be reduced by averaging the points.

FIG. 2C illustrates first portion 2200 modeled in an FEM simulator as in FIG. 1C. Alternatively, a model of second portion 26 may be used. In FIG. 2C, the same steps taken and applied in the FEM simulator may be taken in FIG. 2C. The difference in the depicted embodiment is that the empirical data set entered to define boundary 18 is the data set of average points, or areas of deformation created by the CMM in the steps of FIG. 2B.

Figure 3:
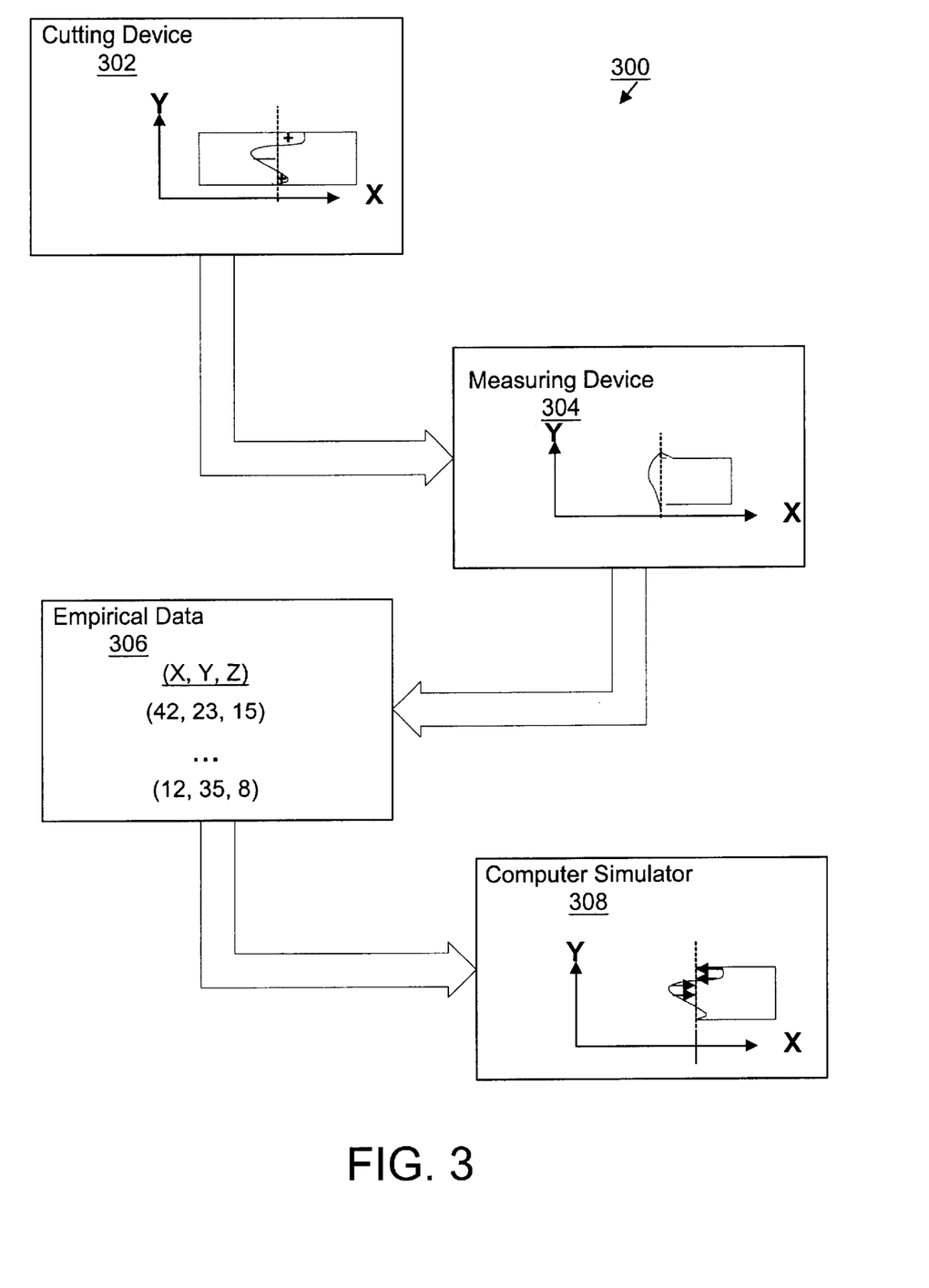
FIG. 3 is a block diagram illustrating one embodiment of a system for determining the residual stress within an elastic object.

Referring now to FIG. 3, a system 300 within the scope of present invention is illustrated. The system 300 comprises a cutting device 302, a measuring device 304, empirical data 306, and a computer simulator 308.

The cutting device 302 is used to divide the object 10 along path 12. Preferably, the cutting device 302 secures the object 10 before, during, and after making the cut. The cutting device 302 should preferably cut as narrow a path 12 through the object 10 as possible. Preferably, the path 12 follows a plane. Therefore, the cutting device should be able to make a substantially straight cut. The cutting device 302 should operate such that a minimal amount of residual stress is introduced within the object 10 along the first free surface 24 and second free surface 28. Various forms of cutting devices 302 may be used including a wire electric discharge machine (wire EDM), laser, water jet, and other like devices.

The measuring device 304 collects information about the contour 18 of the portion 20. The measuring device identifies where points or areas along a free surface 24,28 or contour 18 are located in relation to a coordinate axes system. Generally, an x, y, z coordinate system is used. The portion 20 is positioned within the coordinate system and the measuring device 304 makes its measurements. Preferably, the measuring device 304 measures the position of as small an area as possible. The smaller the area, or point, the more accurate the resulting residual stress calculation. One example of a measuring device 304 is a coordinate measuring machine (CMM). As mentioned above, this device 304 measures by using a probe and is generally accurate to within 0.0001 inches. CMM's are widely used and relied upon in engineering fields.

Preferably, the measuring device 304 stores the measured point locations in an empirical data set. The measuring device 304 may store them directly on some form of digital media such as a disk drive, digital tape, or the like. Alternatively, the measuring device 304 may interface with a general purpose computer to store the measurements.

Referring still to FIG. 3, the system 300 includes a computer simulator 308. The simulator 308 is used as a numerical analysis tool. The computer simulator 308 allows for computation of the residual stress along the path 1200. The operations performed by the computer simulator 308 may be performed manually, although it may not be practical to do so. One example of a computer simulator 308 which may be used in the system 300 is a finite element method simulator (FEM simulator). As discussed in detail earlier, the FEM simulator models an object by representing the object as an accumulation of a finite set of interconnected smaller elements. These smaller elements exhibit properties which are similar to those of the object but are on a smaller scale. Linear force relationships among the elements, such as residual stress, may be used to determine force relationships on the object as a whole. Force relationships between elements correlate to physical properties of the object. The computer simulator 308, FEM, is capable of calculating the forces which cause changes in the properties of the elements. Often an FEM simulator is a module which operates on models in a computer aided drafting (CAD) software program.

One of these properties is displacement. If the computer simulator 308 is given a particular displacement for elements in the object 10, then the computer simulator 308 determines which forces caused the displacement. These forces are residual stress data. In an FEM simulator, these changes in displacement properties may be defined as displacement boundary conditions.

Additionally, the computer simulator 308 may tally, format, and report the results of residual stress data. For example, the residual stress forces acting along contour 18 may be presented as a color coded graphic display in which red and yellow indicate high amounts of residual stress while blue and green indicate low amounts of residual stress. Alternatively, other reports and tabulations may be made available to the analyst.

An analyst may then use the residual stress data to determine engineering or manufacturing changes necessary due to the residual stress within the object. Knowing the residual stress helps an analyst determine when the object may fail when the object is used. Determining the residual stress may be particularly useful for metallic welds. The residual stress within an weld may indicate when the weld will crack and fail and where the crack and failure points are likely to be. The ability to determine the residual stress within a weld allows the analyst to change how the weld is formed, or add back up structural support to compensate for the structural weaknesses of the weld. The size and composition of metallic welds may make determining the residual stress very difficult using alternative methods such as hole drilling. However, using the present invention metallic welds may tested for residual stress in a simple, straight forward manner.

In FIG. 3, the system 300 is arranged with components in the order in which the components or devices may be used within the present invention. Arrows indicate the flow through the system 300 of one performing the present invention. First, the cutting device 302 is used to cut along path 12. Then, the contour 16 of portion 20 is measured using the measuring device 304. Next, the measurements are collected as empirical data 306. And finally, the computer simulator 308 is used to determine, from the empirical data 306, the residual stress along path 12.

Figure 4:
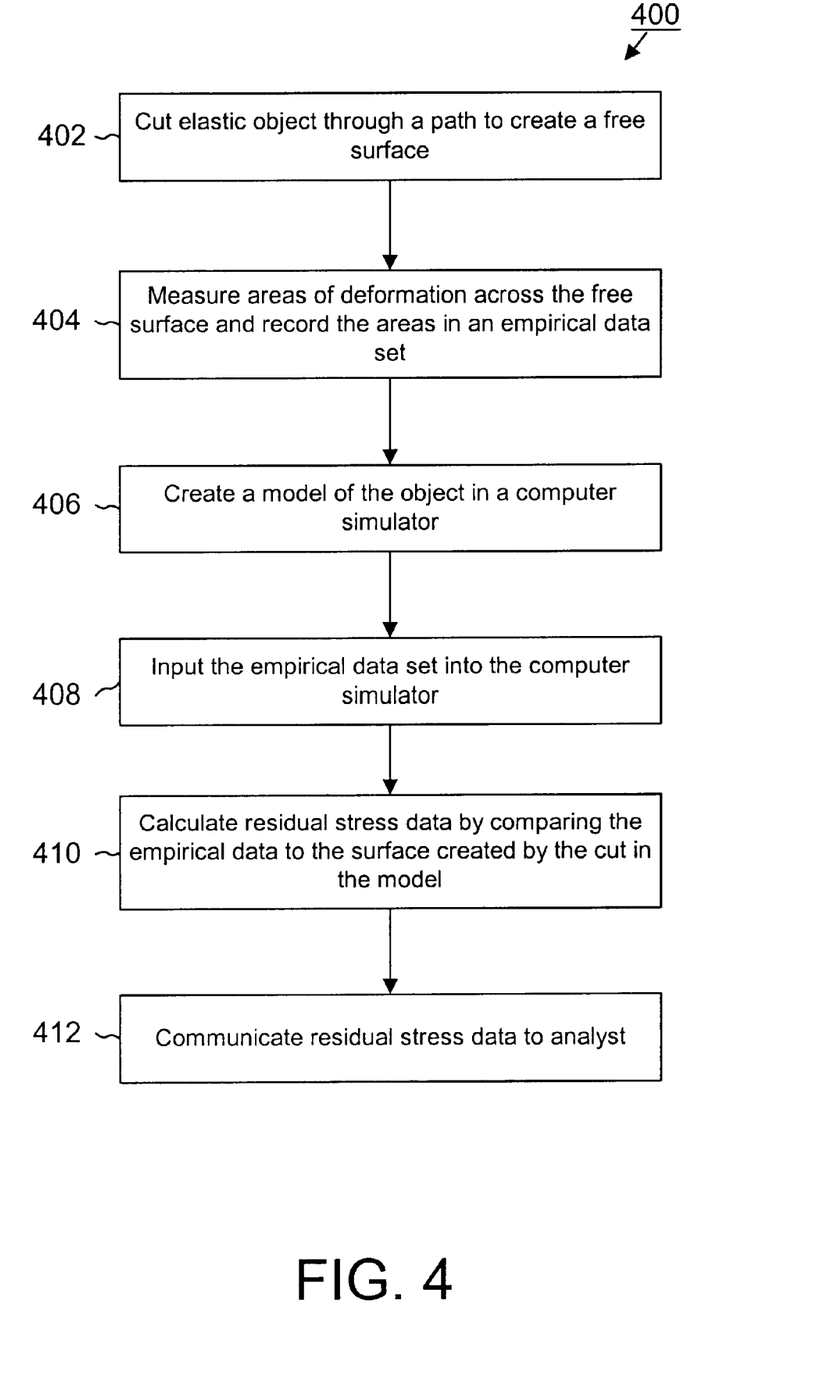
FIG. 4 is a flow diagram of one embodiment of a method for determining the residual stress within an elastic object.

FIG. 4 illustrates a flow diagram of one embodiment of a method 400 for determining the residual stress within an elastic object. In step 402 an elastic object is cut through path 12. The cut creates new free surface 16, or contour 16. The elasticity and residual stress along path 12 cause the free surface 16 to deform.

In step 404, a measuring device 302 is used to measure areas of deformation across the new free surface 16. Preferably, the measuring device 302 is a coordinate measuring machine (CMM). The areas of deformation may be recorded as coordinate points in an empirical data set 306.

In step 406, a model 2000 of one of the cut portions 20 of the object 10 is created in a computer simulator 308. Preferably, the computer simulator 308 is an FEM simulator. The FEM simulator 308 is capable of determining which forces act on a modeled portion 2000 based on defined boundary conditions. The model portion 2000 may be modeled having no residual stress.

In step 408, the empirical data set 306 is entered into the computer simulator 308. The empirical data 306 may be entered as a displacement boundary condition in which the signs of the points in relation to path 12 have been reversed. Then, in step 410, the FEM simulator 308 uses the displacement boundary condition to determine the stress within portion 2000 which caused the displacement of each element. The determined stress is the residual stress normal to the path 12. This residual stress may then be compiled into residual stress data and presented to an analyst in step 412.

Prior to step 412, an embodiment of the present invention may include validating the residual stress data by conducting neutron diffraction analysis on the object. In neutron diffraction analysis the strain of the material at points along contour 18 is determined by shooting neutrons at the contour 18 and measuring how they diffract. From the strain an analyst, generally with the aid of a computer, may multiply the strain by the modulus of the material forming the object to obtain the stress. An analyst may desire to perform neutron analysis on the portion 2000 to validate the residual stress data from method 400. However, diffraction analysis is slow, complex, expensive in terms of time and money, and generally requires experts to properly conduct the analysis. Method 400 provides very similar results in a simple, quick and inexpensive manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for determining the residual stress within an elastic object for use by an analyst, the method comprising:
   cutting an elastic object through a path to create a portion having a free surface;
   measuring a plurality of points across the free surface to define a contour and recording the points in an empirical data set;
   creating a model of the portion of the object in a computer simulator;
   inputting the empirical data set into the computer simulator;
   calculating residual stress data across the free surface as a function of a change in properties of elements of the model portion along the path and properties defined by the points in the empirical data set of the portion along the path; and
   communicating the residual stress data for use by an analyst.

2. A method as in claim 1, wherein the path comprises a plane.

3. A method as in claim 1, wherein the computer simulator comprises a finite element method simulator.

4. A method as in claim 3, wherein inputting comprises defining a displacement boundary condition using the points in the empirical data set.

5. A method as in claim 4, wherein the points in the empirical data set comprise positions having an opposite sign from the original measured sign.

6. A method as in claim 1, wherein the residual stress comprises a normal stress component which represents the residual stress normal to the free surface.

7. A method as in claim 1, wherein the residual stress comprises a transverse normal stress component which represents the residual stress in a y-direction parallel to the free surface.

8. A method as in claim 1, wherein the residual stress comprises a transverse normal stress component which represents the residual stress in a z-direction parallel to the free surface.

9. A method as in claim 1, wherein measuring comprises identifying an x-coordinate, a y-coordinate, and a z-coordinate which is unique for each point along the surface.

10. A method as in claim 1, wherein a device for cutting the object is selected from the group consisting of a wire electric discharge machine, a laser, and a water jet.

11. A method as in claim 1, wherein the object comprises a metal alloy.

12. A method as in claim 1, wherein the object comprises a non-crystalline material.

13. A method for determining the residual stress within an elastic object for use by an analyst, the method comprising:
   cutting an elastic object through a plane to create a first free surface and a second free surface;
   measuring areas of deformation of the object across the first free surface and the second free surface;
   calculating average areas of deformation from the areas of deformation of the first free surface and the areas of deformation of the second free surface and recording the average areas of deformation in an empirical data set;
   creating a model of a first portion of the object in a computer simulator, the first portion having the first free surface;
   inputting the empirical data set into the computer simulator;
   calculating residual stress data as a function of the difference between the properties of the first portion along the plane and properties defined in the empirical data set of the object along the plane; and
   communicating the residual stress data for use by an analyst.

14. A method as in claim 13, wherein measuring areas of deformation further comprises measuring the location of a plurality of points on the first free surface and the location of a corresponding plurality of points on the second free surface.

15. A method as in claim 13, further comprising validating the residual stress data by conducting neutron diffraction analysis on the object.

16. A method as in claim 13, wherein the object comprises a metallic weld.

17. A system for determining the residual stress within an elastic object for use by an analyst, the system comprising:
   a cutting device configured to form a cut along a plane through an elastic object;
   a measuring device configured to measure the location of points on the surface of the cut and storing the measurements in an empirical data set; and a computer simulator configured to model the object and apply the empirical data set to directly calculate residual stress.

18. A system as in claim 17, wherein the computer simulator comprises a model of the object which simulates the physical characteristics of the object and programmed to;

calculate a force which causes displacement of points along the plane to points in the empirical data set; and communicate the force as the residual stress at each point along the plane.

19. A system as in claim 18, wherein the force comprises a normal component and a transverse component and further wherein the normal component comprises a difference along an x-axis.

20. A system as in claim 17, wherein the cutting device comprises a wire electric discharge machine.

21. A system as in claim 17, wherein the computer simulator comprises a finite element simulator.

22. A system as in claim 17, wherein the measuring device comprises a coordinate measuring machine.

* * * * *